United States Patent [19]

Shaw et al.

[11] 3,980,766

[45] Sept. 14, 1976

[54] ORALLY ADMINISTERED DRUG COMPOSITION FOR THERAPY IN THE TREATMENT OF NARCOTIC DRUG ADDICTION

[75] Inventors: Irving F. Shaw, East Rockaway; Jerome Berk, New Rochelle, both of N.Y.

[73] Assignee: West Laboratories, Inc., Long Island City, N.Y.

[22] Filed: Jan. 27, 1975

[21] Appl. No.: 544,360

Related U.S. Application Data

[60] Division of Ser. No. 387,712, Aug. 13, 1973, Pat. No. 3,885,027, which is a continuation-in-part of Ser. No. 133,344, April 12, 1971, abandoned.

[52] U.S. Cl. .................................. 424/10; 424/80; 424/180; 424/311; 424/330; 424/361; 424/362
[51] Int. Cl.² ...................................... A61K 31/135
[58] Field of Search ............. 424/10, 311, 330, 361

[56] References Cited
UNITED STATES PATENTS

| | | | |
|---|---|---|---|
| 3,173,835 | 3/1965 | Weiner et al. ...................... | 424/361 |
| 3,551,133 | 12/1970 | Sprayberry et al. ................ | 424/361 |
| 3,555,151 | 12/1966 | Kaplan et al. ...................... | 424/361 |

FOREIGN PATENTS OR APPLICATIONS

| | | | |
|---|---|---|---|
| 1,601,446 | 10/1970 | France ............................... | 424/361 |

OTHER PUBLICATIONS

Remington's Practice of Pharmacy, (1961), pp. 446–448.
Carnie, Chemical Abstracts, 62;8933a, (1965).
Laszlo, Chemical Abstracts, 56:8854–8855, (1962).
Nishide, Chemical Abstracts, 57:10546a, (1962).

*Primary Examiner*—Norman A. Drezin
*Attorney, Agent, or Firm*—Robert I. Pearlman

[57] ABSTRACT

Drugs which are suitable for such therapy in treatment of narcotic drug addiction by oral use, e.g., methadone, are formulated to prevent injection abuse through concentration of the active component in aqueous solution by incorporating in a solid dosage or tablet form of such drug an ingestible solid having thickening properties which causes rapid increase in viscosity upon concentration of an aqueous solution thereof.

2 Claims, No Drawings

ORALLY ADMINISTERED DRUG COMPOSITION FOR THERAPY IN THE TREATMENT OF NARCOTIC DRUG ADDICTION

CROSS REFERENCE TO RELATED APPLICATIONS

This application is a divisional of Ser. No. 387,712, filed Aug. 13, 1973, now U.S. Pat. No. 3,885,027, which in turn is a continuation-in-part of Ser. No. 133,344, filed Apr. 12, 1971 now abandoned, both for the instant inventors.

BACKGROUND OF THE INVENTION

In attempting to combat the problem of narcotic addiction and particularly addiction to heroin, considerable attention has been given in recent years to oral administration of drugs which have the effect of greatly reducing or abolishing narcotic hunger and blocking the euphoriant action of the heroin or other addictive drugs. Particularly encouraging results have been achieved when using the drug methadone in the form of the free base or acid salts thereof such a methadone hydrochloride. While methadone itself has some addictive tendencies when administered orally, it does not have euphoriant properties and has been found effective when treating addicts in blocking both narcotic hunger and the euphoriant action of other addictive drugs.

The accepted procedure in the oral administration of methadone or its acid salts has been to incorporate the same into a powder or water soluble tablets of dosage unit size, dissolving in a small quantity of orange juice or other fruit juice and having the patient drink this juice solution. The effectiveness of treatment is largely dependent upon an established treatment schedule being adhered to; and when treating out-patients, they are provided with a limited number of doses with specific instructions as to frequency of use.

In preparing tablets containing methadone or its acid salts for use in the manner described, it has been the practice to provide a readily water soluble composition so that the powder or tablets can be quickly and easily dissolved in fruit juice for administration. A problem with powders or tablets of the type heretofore available, however, is that they can also be dissolved in plain water to provide a solution which can be filtered fairly easily, and concentrated by evaporation to produce an aqueous residue sufficiently rich in methadone to be attractive to addicts when administered by injection as a substitute for their habitual addictive drugs. Drug addicts have been quick to recognize this possibility and the need for guarding and policing supplies of methadone and its acid salts have tended to limit the more extended use of these drugs in oral maintenance therapy.

Conventional methadone hydrochloride tablets are also potentially hazardous if a quantity of tablets are accidentally ingested. In fact, several fatalities have been reported due to out-patients' supplies of methadone hydrochloride being found and ingested by children.

THE INVENTION

In attacking the problems above mentioned, it has been found that ingestible solids having thickening capability as components of a drug composition for maintenance therapy could help prevent injection abuse by increasing viscosity of a solution of a composition during attempted evaporation so that separaton of the therapeutic agent in sufficiently concentrated form to permit its use by injection would become extremely difficult without highly specialized equipment. In forming compositions and tablets in accordance with the invention, one or more additives are incorporated which have the effect of deterring concentration by causing a rapid increase in viscosity during evaporation of an aqueous solution of the composition. For this purpose various ingestible solids having thickening capability can be employed including, for example, sugars or sugar derived alcohols, such as lactose, sucrose, mannitol, sorbitol, and the like, and polymeric materials, such as starches, microcrystalline cellulose, sodium caboxymethyl cellulose, methylcellulose, ethyl cellulose, carrageenin, gum tragacanth, gum acacia, polyvinylpyrrolidone, etc. Such additives or adjuvants are preferably present in the proportion of about 0.5 to 1.5 grams per tablet containing the normal unit dose of therapeutic agent (40 mg in the case of methadone hydrochloride). Expressed in another way, the weight ratio of this type of additives to the therapeutic agent should be in the range of about 10 to 1 to 40 to 1.

With these ingestible solid additives or adjuvants present in the composition, attempts at evaporation of an aqueous solution in an effort to produce an aqueous concentration of the therapeutic agent, sufficient to produce a "high" upon injection, will produce a highly viscous concentrate incapable of being handled by a syringe.

Separate investigation into the solubility of methadone in the general pH range of 6 to 9 gave results as shown in the following tabulation:

| SOLUBILITY OF METHADONE CALCULATED AS THE HYDROCHLORIDE | | |
| --- | --- | --- |
| pH | % Soluble | mg/5 ml |
| 6.4 | 4.4 | 220 |
| 7.0 | 1.0 | 50 |
| 7.05 | 0.85 | 42.5 |
| 7.10 | 0.57 | 28.5 |
| 7.50 | 0.20 | 10 |
| 7.60 | 0.12 | 6 |
| 8.10 | 0.03 | 1.5 |
| 8.8 | <0.01 | <0.5 |

In this connection, it should be noted that one attempting to achieve a "high" by injection of methadone solution will need about 20 mg of methadone in 1 to 5 ml of water. From the above table, it will appear that at a pH of 7 or lower, an aqueous solution of sufficient strength for injection to achieve a "high" can be prepared, but above pH 7 it becomes increasingly difficult to prepare a solution of sufficient strength and at a pH above 7.50 the solubility of methadone becomes so low as to completely frustrate its improper use by injection.

In view of the foregoing, it is additionally desirable to incorporate in a drug formulation for oral administration in maintenance therapy treatment of narcotic addiction, a component which will induce precipitation of a major portion of the therapeutic agent if the composition is dissolved in water and the solution is then concentrated, while at the same time permitting full dissolution in orange juice or comparable acidic media which do not permit of injection. Essentially, the reduced solubility may be attained either by a composition which produces a pH of about 7.5 to 10 directly upon dispersion in water, or by a composition which upon initial dispersion produces a pH of at least 6 which then increases to pH 7.5 or more upon concentration; or by a component which will form a salt with the therapeutic agent which is soluble at an acidic pH but has markedly reduced solubility at a substantially neutral or alkaline pH.

Typical ingestible solids which provide an alkaline pH in aqueous solution include soluble alkali metal and alkaline earth metal carbonates, bicarbonates, phosphates, and acid phosphates. Of these, the bicarbonates, and particularly sodium bicarbonate, are considered preferable since, as earlier mentioned, the evolution of $CO_2$ during heating of an aqueous solution causes the pH to drift progressively higher during attempts at evaporation.

When $NaHCO_3$ is used as the pH regulating additive, additional amounts can be employed together with a stoichiometrically equivalent amount of a solid food acid, such as tartaric acid and the like.

Typical examples of ingestible solids which can form insoluble salts of the therapeutic agent at a substantially neutral or alkaline pH while at the same time being soluble at an acid pH are alkaloid precipitating agents such as tannic acid and picrolonic acid. When the composition contains this type of additive for reducing solubility of the therapeutic agent in water, it can still be advantageous to employ a disintegrating agent, suitably in the form of sodium bicarbonate in combination with a solid food acid as above described.

The amount of pH controlling component to be incorporated in the composition will vary to some extent with the particular therapeutic agent and the intended dosage thereof. By way of illustration, when methadone hydrochloride is the therapeutic agent, a tablet or other solid dosage unit, generally containing 40 mg of methadone hydrochloride, is dissolved in about three to four ounces of water, orange juice or other acidic (pH 5 or lower) drink before being taken by the patient. On the other hand, a person seeking to recover an injectable form of methadone from such solid dosage form would dissolve the same in a minimum amount of water, probably less than 10 ml since larger amounts of water would merely complicate efforts to concentrate the drug. Thus, the amount of pH controlling agent solid dosage unit should be sufficient to provide the desired pH control when a dosage unit is dissolved in about 10 ml of water.

A component which acts, instead, by forming an insoluble salt at a substantially neutral pH should be present in at least the stoichiometric amount to react with the methadone or other therapeutic agent in the composition.

While each of the type additives above described can be useful individually in curbing the misuse of drug compositions prepared for oral administration in maintenance therapy, it must be borne in mind that the drive of drug addicts to satisfy their hunger for drugs can make them extremely resourceful in devising means of preparing an injection. For this reason, it is desirable to employ a plurality of deterrents. Preferred compositions will include, in addition to the methadone or other drug, at least one pH control or salt forming component which will precipitate the therapeutic agent, and one or more of the viscosity control components or thickening agents.

In the preparation of tablets or other dosage units of the drugs, it will be understood that, in addition to the special additives or adjuvants above described, there will be present the normal type of solid adjuvants including agents such as zinc stearate which facilitate mold release in the formation of tablets. Adjuvants of the composition can also include conventional coloring agents and/or flavoring agents. It is considered preferable, however, to omit flavoring agent since the bitterness imparted by the therapeutic agent further tends to discourage accidental ingestion, while being offset during administration by the fruit juice or other acidic drink normally employed for dissolving the drug in maintenance therapy in treatment of narcotic drug addiction.

The following examples will provide a fuller understanding of the invention, but it is to be understood that these examples are given by way of illustration and not of limitation.

EXAMPLE I

The ingredients and manufacturing method for producing a batch of about 20,000 methadone hydrochloride tablets are given below.

| | | |
|---|---|---|
| Methadone Hydrochloride USP Powder | 800 | grams |
| Mannitol Powder | 5,720 | '' |
| Lactose | 5,800 | '' |
| Corn Starch Powder | 8,200 | '' |
| Polyvinylpyrrolidone | 340 | '' |
| Tartaric Acid | 5,000 | '' |
| Methylcellulose | 100 | '' |
| Ethylcellulose | 100 | '' |
| Zinc Stearate | 200 | '' |
| Microcrystalline Cellulose | 1,400 | '' |
| Sodium Bicarbonate | q.s. 39,000 | '' |

The indicated quantities of methadone hydrochloride, mannitol, lactose, corn starch, polyvinylpyrrolidone, and tartaric acid are mixed until homogeneity is achieved. The proper quantity of granulating solution consisting of 50% methanol and 50% demineralized water is added. The resulting wetted mass is screened and evenly spread on paper lined trays, and dried at 100°–110°F. in suitable ovens. Drying is considered complete when the moisture content is less than 0.5% maximum. The material is then screened again. This screened mass is weighed and then transferred to a mixing vessel to which are added the proper quantities of methylcellulose, ethylcellulose, zinc stearate, microcrystalline cellulose; finally enough sodium bicarbonate is added to bring the mass to the required total weight. This is then mixed until homogeneity is achieved. The resultant mixture is assayed and then transferred to a compressing machine on which tablets are produced in accordance with the specifications, to contain 40 mg of methadone hydrochloride.

The same formula can be prepared in powder form with or without the zinc stearate by simple mixing without granulating. Alternatively, the granules can be prepared for dispensing as such by omitting the compression procedure. Tablets containing from 5 to 100 mg of methadone hydrochloride can be formed from the identical composition according to therapeutic need.

A tablet, prepared as above described, when placed in about 4 ounces of orange juice, effervesces spontaneously and disintegrates completely within about three minutes. Slight stirring will speed disintegration and assure a uniform suspension. Drinking of a suspension thus prepared by a patient on maintenance therapy is found to be equally as effective as similar suspensions made with 40 mg of U.S.P. methadone hydrochloride or other commercially available 40 mg tablets.

One tablet containing 40 mg was added to 4 ounces of water (about 120 ml) at room temperature. The tablet was permitted to effervesce spontaneously. Dispersion was complete within three minutes. The suspension was stirred to make it essentially uniform and passed through a Whatman number 31 filter paper until the filtrate was clear. The pH of the filtrate was 6.7. Analysis showed approximately 0.35 mg/ml methadone hydrochloride, substantially the theoretical amount. This very dilute solution could be passed through a syringe, but would be of little value for illicit parenteral administration because of the extreme dilution.

The filtered solution was then concentrated by evaporation in a constant stream of air with gentle heating by means of a hot plate. When the volume of the solution was brought down to 20 ml, corresponding to a "theoretical" methadone hydrochloride content of 2 mg/ml, a sludge of amorphous material formed in the container. Analysis showed practically no methadone hydrochloride in the liquid portion, less than 0.1 mg/ml. The pH of the filtrate was 8.8.

It is significant that the excess of sodium bicarbonate in the composition of this example permitted a substantially neutral pH at the initial dissolution, permitting the methadone to remain in dilute solution when the tablet was dissolved in water. However, attempts to concentrate the solution caused the indirect effect of raising the pH. This use of the latent alkalinity of sodium bicarbonate to prevent abuse in replacement therapy is a prominent feature of this invention. With increased excess of sodium bicarbonate if desired, it is possible to render the methadone less soluble, so that filtered solutions will immediately show reduced methadone content.

Another tablet containing 40 mg of methadone hydrochloride was added to 10 ml of water. In this case, the disintegration time increased compared with the use of 120 ml of water. Upon stirring the solution and allowing it to settle (the settling took several hours), 8 ml of turbid solution could be withdrawn. The analysis of this solution showed less than 0.1 ml/ml of methadone.

By way of comparison, a commercial tablet, salmon colored, quadrisected, containing 40 mg methadone hydrochloride, and weighing 1.70 grams was placed in 120 ml of water. The tablet expanded in volume and dissolved slowly in water leaving a fine sediment at the bottom of the container. The pH of the solution was 5.3; this pH remaining constant over several minutes. The "solution" was filtered through an analytical grade of filter paper, leaving a heavy orange residue containing practically no methadone. The filtrate was carefully evaporated on a hot plate to 10% of its volume, during which time the pH decreased to 5.1. Further evaporation gave an orange film, weighing 0.16 gram. The film was soluble in 2.5 ml of water to give an opaque orange solution, pH 4.6, containing the 40 mg of methadone, an unapproved injectable pharmaceutical form.

The acute oral toxicity of the methadone hydrochloride in the composition of Example I is found to be significantly lower than the acute oral toxicity of methadone hydrochloride U.S.P.

EXAMPLE II

A tableting formulation of methadone hydrochloride is prepared using the following ingredients and formed into tablets each containing 40 mg of methadone hydrochloride:

| | | |
|---|---|---|
| Methadone HCl | 0.5 | parts |
| Lactose | 6.0 | " |
| Mannitol | 2.0 | " |
| Corn Starch | 2.5 | " |
| Disodium Phosphate | 0.25 | " |
| Sod. carboxymethylcellulose | 0.5 | " |
| Methyl Cellulose | 0.5 | " |
| Sod. Saccharin | 0.2 | " |
| Zinc Stearate | 0.75 | " |

A tablet thus prepared was dispersed in 120 ml of distilled water and gave a pH of 7.8. Upon filtration and concentration to 10 ml, a viscous gummy mass resulted, of substantially the same pH. The concentrated solution could not be drawn up into a syringe with a number 18 needle. Analysis of a drop of clear liquid that separated from the gummy mass showed less than 1 mg/ml methadone.

Tablets of this composition disperse readily in 4 ounces of orange juice, with complete methadone solubility. The same formula can be suitably used to prepare a capsule dosage form.

EXAMPLE III

A tableting composition similar to that described in Example I but including 2400 gm of tannic acid, i.e., three times the weight of methadone hydrochloride, was prepared and formed into 40 mg tablets.

When one of these tablets (containing 40 mg of methadone hydrochloride and 120 mg of tannic acid) was dispersed in 120 ml of water, and filtered, the pH was 6.7, and the filtrate contained about 0.02 mg of methadone hydrochloride per ml. The theoretical amount should be about 0.33 mg per ml indicating substantial removal from solution.

When another of these tablets was dissolved in 4 ounces of orange juice, pH 4, and filtered, the solution analyzed 0.33 mg/ml methadone HCl, the theoretical amount, indicating that availability in acid solution was unimpaired.

EXAMPLE IV

Another chemical compound which has found some use as a drug in maintenance therapy is propoxyphene (4 dimethylamino- 3-methyl-1, 2-diphenyl 2-butanol propionate). The solubility characteristics of propoxyphene are favorable for pH control, as shown below:

| SOLUBILITY OF PROPOXYPHENE CALCULATED AS THE HYDROCHLORIDE | | |
|---|---|---|
| pH | % Soluble | mg/10 ml |
| 6 | >1.0 | >100 |
| 6.5 | 0.83 | 83 |
| 6.85 | 0.23 | 23 |
| 7.25 | 0.09 | 9 |
| 8.0 | 0.01 | 1 |
| 8.5 | 0.005 | 0.5 |
| 9.0 | <0.002 | <0.2 |

A tableting composition was prepared, using the following ingredients, and formed into tablets each containing 100 mg of propoxyphene hydrochloride:

| | | |
|---|---|---|
| Propoxyphene Hydrochloride | 2,000 | grams |
| Mannitol | 5,000 | '' |
| Milk Sugar | 5,500 | '' |
| Corn Starch | 8,200 | '' |
| Polyvinylpyrrolidone | 400 | '' |
| Methylcellulose | 100 | '' |
| Ethylcellulose | 100 | '' |
| Tartaric Acid | 5,000 | '' |
| Zinc Stearate U.S.P. powder | 200 | '' |
| Microcrystalline cellulose | 1,400 | '' |
| Sodium Bicarbonate | q.s. 40,000 | '' |

A tablet was dissolved in 120 ml water and gave a pH of 6.5. The solution was filtered and analyzed for propoxyphene. The filtrate contained the approximate "theoretical" amount, 0.8 mg/ml. The filtrate was then evaporated at low temperature with the aid of a stream of air, causing the pH to rise rapidly. When half the water was gone the pH was 8.7. When only 10 ml of water was left, the pH was 9.0. Analysis showed that the cconcentration of propoxyphene in solution when only 10 ml of solution remained, was substantially nil, less than 0.1 mg/ml. In other experiments in which the solution was evaporated by heating alone or by allowing to stand at room temperature alone, similar results were obtained, indicating, that the method used to concentrate the solution did not affect the results significantly. Tablets containing from 25 to 200 mg of propoxyphene hydrochloride can be formed from the identical composition according to the therapeutic need.

While the disclosure has been aimed primarily at maintenance therapy in the treatment of narcotic drug addiction, the ultimate goal of withdrawal can also be served by means of anit-addiction and antagonist treatment. The same principles taught herein can be used to formulate anti-addiction or antagonist drugs such as naloxone, cyclazocine, and thebaine, for example, thereby insuring that the compositions be used for therapy by oral administration.

Other therapeutic agents in addition to those described herein may be found useful in the treatment of narcotic drug addiction, and it is to be understood that the principles of the present invention for deterring injection abuse by incorporating a thickening agent, or precipitating and thickening agents in the composition can be employed with other amine (or substituted amine) containing therapeutic agents useful in the treatment of narcotic drug addiction, the hydrochloride salt form of which is soluble in water but essentially insoluble in alkaline solution.

Various changes and modifications in the compositions herein disclosed may occur to those skilled in the art, and to the extent that such changes and modifications are embraced by the appended claims, it is to be understood that they constitute part of the present invention.

We claim:

1. A solid composition for the oral treatment of narcotic addiction which is dispersible for dissolution before ingestion, said composition comprising:
   a. an effective amount of methadone or its acid salts, and
   b. an ingestible solid in a weight ratio of 10:1 to 40:1 per part of methadone in an amount sufficient to cause a rapid increase in viscosity during evaporation of an aqueous solution of the composition, wherein said ingestible solid is lactose, sucrose, mannitol, sorbitol, starch, microcrytalline cellulose, sodium carboxymethyl cellulose, methylcellulose ethylcellulose, carrageenin, gum tragacanth, gum acacia or polyvinylpyrrolidone.

2. The composition of claim 1 which further contains $NHCO_3$ as a precipitating agent.

* * * * *